United States Patent [19]

Child

[11] 4,210,409
[45] Jul. 1, 1980

[54] SOLENOID OPERATING PUMP

[75] Inventor: Frank W. Child, Eagle Bend, Minn.

[73] Assignee: Child Laboratories Inc., Eagle Bend, Minn.

[21] Appl. No.: 907,809

[22] Filed: May 19, 1978

[51] Int. Cl.² .................... F04B 17/04; F04B 21/04; F04F 7/00
[52] U.S. Cl. .................... 417/241; 417/417; 417/551; 128/DIG. 3
[58] Field of Search .................... 417/417, 551, 241; 92/162 R, 162 P; 128/DIG. 3

[56] References Cited

U.S. PATENT DOCUMENTS

| | | | |
|---|---|---|---|
| 110,177 | 12/1870 | Ward | 92/162 R X |
| 1,557,224 | 10/1925 | Warner | 417/551 X |
| 1,652,374 | 12/1927 | Price | 92/162 R |
| 2,925,814 | 2/1960 | Vibber et al. | 417/417 X |
| 3,097,366 | 7/1963 | Winchell | 128/DIG. 3 |
| 3,348,489 | 10/1967 | Meyer | 417/417 |
| 3,384,021 | 5/1968 | Perron | 417/417 |
| 3,479,959 | 11/1969 | Christensen | 417/417 |
| 3,771,173 | 11/1973 | Lamb | 128/DIG. 3 |
| 3,791,769 | 2/1974 | Kovaks | 417/417 |
| 3,824,629 | 7/1974 | Shiley | 3/1 |
| 3,835,475 | 9/1974 | Child | 3/1 |
| 4,090,816 | 5/1978 | Takahashi | 417/417 X |

Primary Examiner—Richard E. Gluck
Attorney, Agent, or Firm—Burd, Bartz & Gutenkauf

[57] ABSTRACT

A pump for moving fluid, as blood, having a cylindrical body defining a chamber. A piston movably located in the chamber carries a one-way valve movable to an open position to allow fluid to flow into the chamber and movable to a closed position to pump fluid from the chamber. One or more solenoids operate to reciprocate the piston in the chamber to pump fluid from the chamber. A one-way valve in an inlet passage to the chamber functions to allow the flow of fluid into the chamber and restrict reverse flow of the fluid out of the chamber through the inlet passage.

38 Claims, 12 Drawing Figures

SOLENOID OPERATING PUMP

SUMMARY OF INVENTION

The invention is directed to a pump having a piston movable in response to magnetic forces established by one or more solenoids to move a fluid. More particularly, the pump is used to pump blood to assist the pumping action of a natural heart. The pump can function as a left ventricle assist device locatable in the descending aorta leading from the heart.

The pump includes a body having a pumping chamber. A piston slidably accommodated in the chamber moves fluid out of the chamber. The piston has a core of magnetic material that is surrounded with a cover or skin. One or more solenoids mounted on the body are energized to produce magnetic fields to reciprocate the piston in the pumping chamber. The piston has a central opening allowing the fluid to move through the piston from the inlet side of the chamber to the outlet side of the chamber. A one-way valve associated with the piston operates to provide one way flow of the fluid from the inlet side of the chamber to the outlet side of the chamber. The body has an inlet passage accommodating a first one-way valve for controlling one way flow of fluid into the inlet side of the pumping chamber. The first one-way valve moves to its closed position when the piston moves toward its non-pumping or reverse position. When the piston is moved in its forward or pumping position, the valve carried by the piston is closed so that the fluid in the outlet side of the chamber is moved from the pump chamber. New fluid moves through the inlet passage past the open first one-way valve into the inlet side of the pumping chamber. The pumping action of the piston is a sequence or pulse action that mimics the pumping action of a natural human heart. The pumping rate and pressure of the blood moving through the pumping chamber is controlled by a control for supplying electric power to the solenoids.

The pump is operable to move blood in a manner that simulates the pumping action of a heart. The pump has internal moving parts and a relatively small size and shape which allows the entire pump to be implanted within the body to assist, and, if necessary, replace the pumping function of a natural heart. The pumping piston is enclosed within a housing which prevents leakage of the fluid from the housing and prevents the contamination of the fluid moving through the housing. The piston located in the pumping chamber is free to rotate about its central axis as it reciprocates in the chamber to minimize localized wear and allow blood to wash inside and outside surfaces of the piston. These and other advantages of the pump of the invention are embodied in the pump hereinafter described.

DESCRIPTION OF PREFERRED EMBODIMENTS

Figure 1:
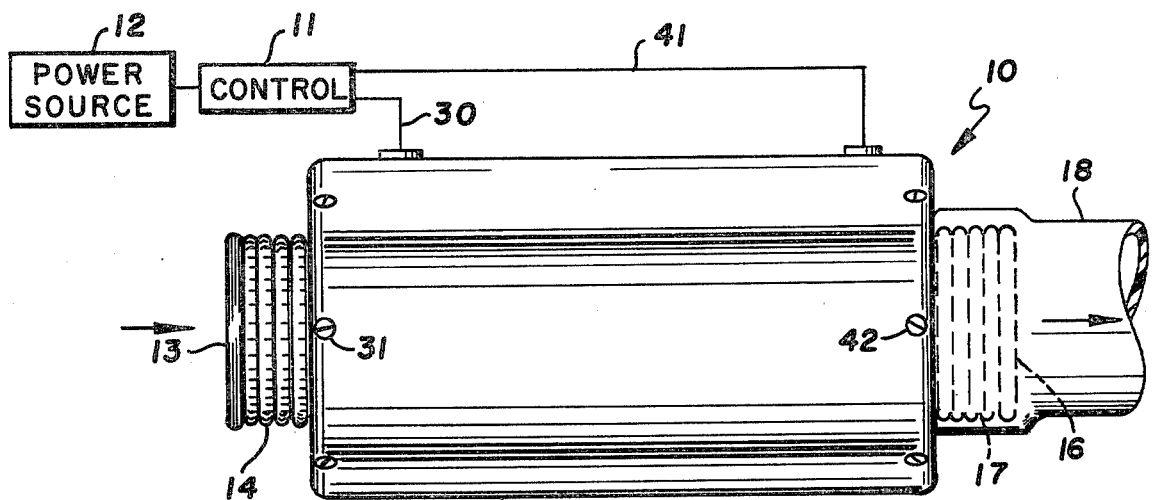
FIG. 1 is a diagrammatic view of the pump of the invention connected to a control and power source.
Figure 2:
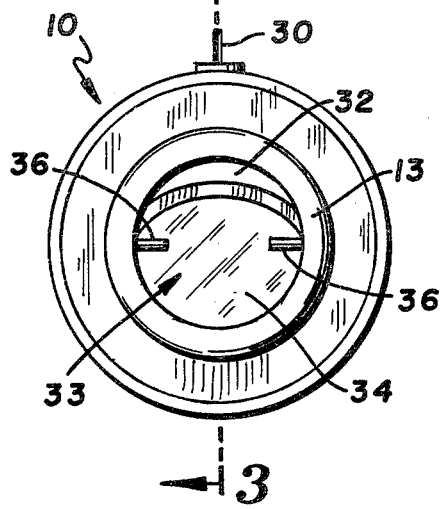
FIG. 2 is an end elevational view of the left end of the pump of FIG. 1.

Referring to FIG. 1, there is shown a first embodiment of the pump of the invention indicated generally at 10 connected to a control 11 powered by a power source 12. Power source 12 can be a battery or an external source of electric power. Control 11 has electronic switching circuits connected with lines 30 and 41 to the solenoids of pump 10, as hereinafter described. Pump 10 is described as a cardiac assist pump as it moves the blood in one direction as indicated by the arrows through the pump in a manner that simulates the pressure and heat or fluctuation of the blood of a natural heart. Pump 10 is suitable for pumping or moving other types of fluids, such as water, oil, and like fluids.

Pump 10 is an elongated cylindrical structure having at one end an inlet collar or sleeve 13. A suturing ring 14 surrounds sleeve 13 and is used to attach tissue, such as an artery or vein, to ring 14. The opposite end of pump 10 has an outlet collar or sleeve 16 carrying a suturing ring 17. A tubular member 18, such as the tissue of an artery or vein, surrounds suturing ring 17 and is attached thereto with suitable sutures. Other types of tubular coupling structure can be used to attach pump 10 to the circulatory system of a human or animal. Suturing rings 14 and 17 are fabric structures which are porous to accommodate the tissue ingrowth. Suturing rings 14 and 17 can be the suturing members as disclosed by Child in U.S. Pat. No. 3,835,475. Other types of suturing members can be used.

Figure 4:
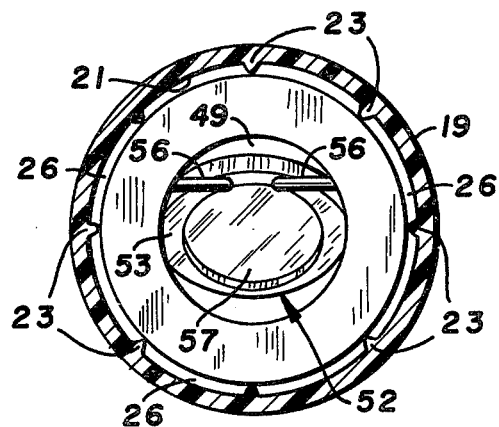
FIG. 4 is a sectional view taken along the line 4—4 of FIG. 3.
Figure 3:
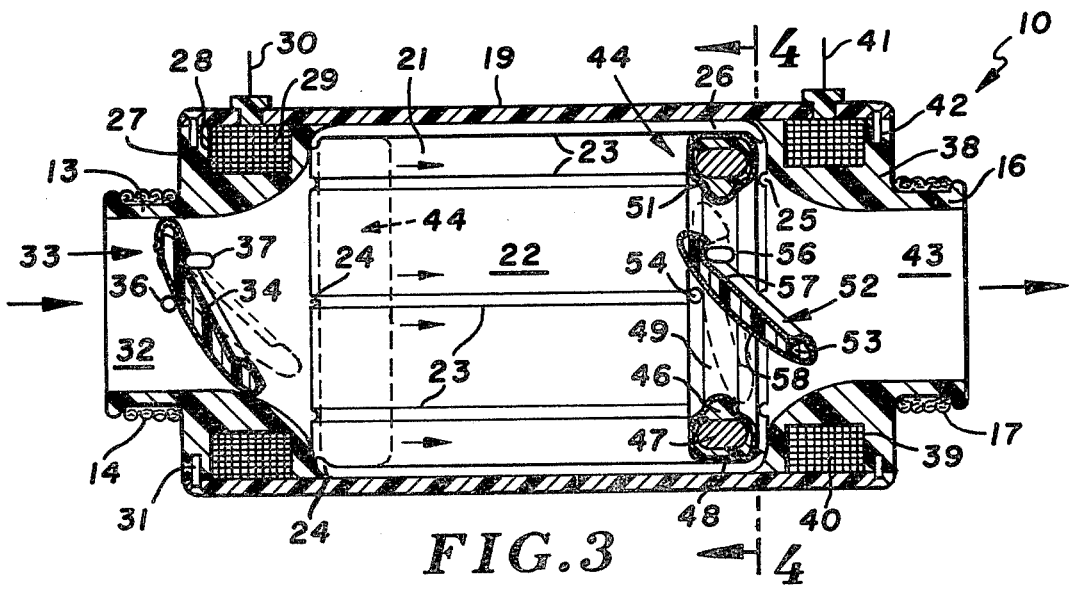
FIG. 3 is an enlarged longitudinal sectional view of the pump of FIG. 1.

Referring to FIG. 3, pump 10 has a cylindrical body or casing 19 having an inside wall 21 surrounding a pumping chamber 22. A plurality of inwardly directed longitudinal vanes or ribs 23 are integral with inside wall 21. As shown in FIG. 4, ribs 23 are circumferentially spaced from each other and extend around inside wall 21. The number of ribs can vary. The opposite ends of ribs 23 terminate in ends or stop projections 24 and 25. Adjacent ribs are separated by an arcuate space or opening 26.

Returning to FIG. 3, a first end member 27 is mounted on one end of body 19. End member 27 fits into the end of body 19 and engages stops 24. Fasteners 31, as bolts, set screws, pins, and the like, fix the position of end member 27 on body 19. Other types of fasteners or connectors can be used to join end member 27 to body 19.

End member 27 has an outwardly open annular groove 28 accommodating a first coil or solenoid 29.

Solenoid 29 comprises wire windings that are connected to control 11 via electrical line 30.

End member 27 has a longitudinal passage 32 accommodating an inlet one-way valve assembly indicated generally at 33. Valve assembly 33 has a valving member 34. Valving member 34 is a generally flat circular disc having a circular recess on the proximal side of the disc. A pair of proximal pivots 36 attached to end member 27 contact disc 34 to provide pivot members for the disc. Distal pivots 37 attach to end member 27 and extend into the recess of the disc to retain the disc in a pivotal relationship with end member 27. Disc 36 has a sliding pivotal motion offset from the center of the disc as it moves from a closed position, as shown in full lines toward an open position as shown in dotted lines. Valving member 34 permits the flow of fluid through passage 32 into pumping chamber 22 and restricts the reverse flow of the fluid from pumping chamber 22 through passage 32.

A second end member 38 is mounted on the second or right end of body 19. Second end member 38 has an annular groove 39 accommodating a second coil or solenoid 40. Electrical conductor line 41 connects solenoid 40 to control 11. Fasteners 42, as set screws, secure body 19 to end member 38. Other types of fasteners can be used to secure body 19 to end member 38.

End member 38 has an outlet passage 43 open to the pumping chamber 22 and extending through collar 16. The inner portion of passage 43 has a cone shape to facilitate the flow of blood from chamber 22 through passage 43.

A piston indicated generally at 44 is located in the pumping chamber 22. Piston 44 has an annular body or ring 46. Body 46 has an annular core 47 of magnetic material, such as iron and an outer cylindrical surface 48. A passage 49 extends axially through the center of body 46. Passage 49 has a diameter that is substantially the same as the diameter of passages 32 and 43. Body 46 has a covering layer or skin 51. Skin 51 can be a hard biologically inert material, such as pyrolitic carbon. The valving members 34 have a similar cover layer or outer skin.

A second one-way valve assembly indicated generally at 52 operatively mounted on annular body 46 functions to selectively open and close passage 49. Valve assembly 52 has a disc type valving member 53 located between pairs of pivot member 54 and 56. Proximal pivots 54 engage the proximal side of valving member 53. As shown in FIG. 4, distal pivot members 56 are secured to the body 46 and extend toward each other. Pivot members 56 have short inwardly turned projections which extend into a central recess in 57 in the distal side of valving member 53. The outer surface of valving member 57 has a pyrolitic carbon skin or covering 58. Pivot members 54 and 56 pivotally mount valving member 53 for movement between open and closed positions offset from the center of valving member 53 and the center of passage 49, as shown in full and broken lines in FIG. 3.

In use, with piston 44 located in a first or dotted position, as shown in FIG. 3, and the valve member 34 in the closed position, solenoids 29 and 40 are energized in a push-pull mode creating a magnetic field which forces piston 44 to move toward end member 38 as indicated by the arrows. Valving member 53 is in the closed position when piston 44 moves toward end member 38. The blood on the front side of piston 44 is forced through chamber 22 and outlet passage 43. Piston 44 causes a reduced pressure in passage 32 which draws fluid through passage 32 into the left side of pumping chamber 22. The outer cylindrical wall 48 of piston 44, being spaced by ribs 23 from the inner wall 22 by spaces 26, allows a limited reverse flow of blood around the outer peripheral surface 48 of the piston. This slight reverse flow around piston 44 provides for lubrication and continuous washing of the piston surfaces. The blood is always moving around piston 44, thereby eliminating pockets and recesses where blood can accumulate and coagulate. Piston 44 moves toward end member 38 until it engages the stop projections 25. Projections 25 allow for limited reverse movement of the blood around piston 44 as the forward side of piston 44 does not move in a tight sealing engagement with end member 38.

The push-pull flux field of solenoids 29 and 40 are reversed, whereby piston 44 is forced back to its initial position adjacent first end member 47. The piston valving member 53 will move to its open position allowing the blood from chamber 22 to flow through the passage 49 of piston 44. Valving member 34 will close, thereby preventing reverse flow of blood through inlet passage 32. The outer peripheral edge of the valving member 34 can be slightly spaced from the inside wall of passage 32 allowing a limited reverse flow around the valving member 34 when it is in a closed position.

The frequency and speed of movement of piston 44 is controlled by the magnetic force fields of the solenoids 29 and 40. Control 11 is operable to control the electrical power supplied to the solenoids, as well as controlling the rate of movement or pulse of piston 44.

Figure 5:
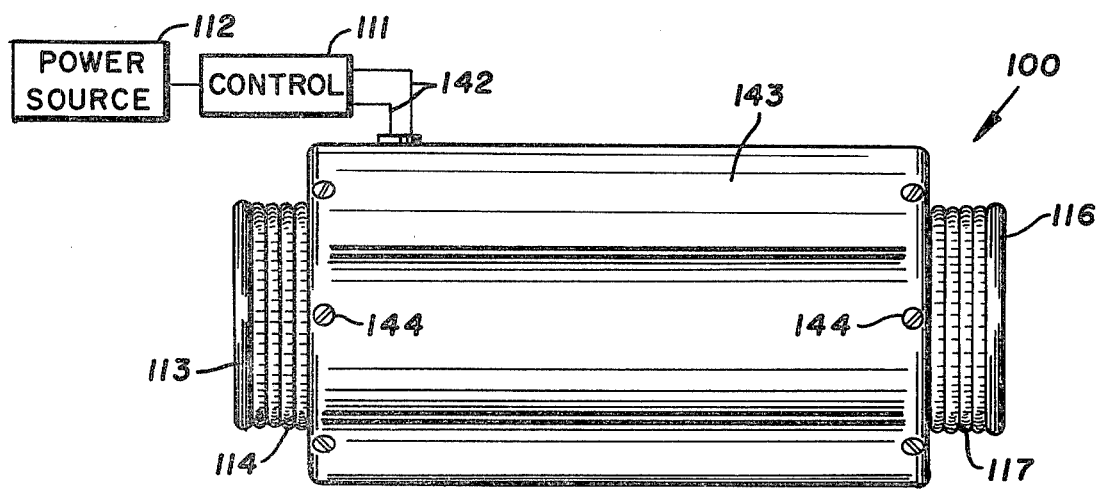
FIG. 5 is a diagrammatic view of a modification of the pump of the invention connected to a control and power source.
Figure 6:
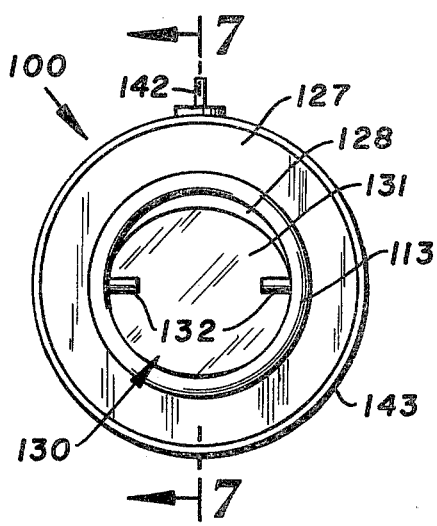
FIG. 6 is an end elevational view of the left end of FIG. 5.

Referring to FIGS. 5–8, there is shown a second embodiment of the pump of the invention indicated generally at 100. Pump 100 is an elongated cylindrical unit operable to pump fluid, as blood, in sequences or pulses. As shown in FIG. 5, pump 100 is connected to a control 111 which is powered by a power source 112. Power source 112 can be a battery or an external source of electric power. Control 111 is an electronic switching circuit connected with lines 142 to a solenoid 141 of the pump, as hereinafter described.

Pump 100 has an inlet collar or sleeve 113 accommodating a suturing ring 114. Collar 113 projects longitudinally from the left end of the pump, as shown in FIG. 5. The opposite end of pump 100 has an outlet collar or sleeve 116 carrying a suturing ring or collar 117. Tubular members (not shown), such as the tissue of an artery or vein or a fabric or plastic tubular member, is adapted to fit over the suturing rings 114 and 117 and attach thereto with suitable sutures. Other types of tubular coupling structure can be used to attach the pump to the circulatory system of a primate or animal.

Figure 8:
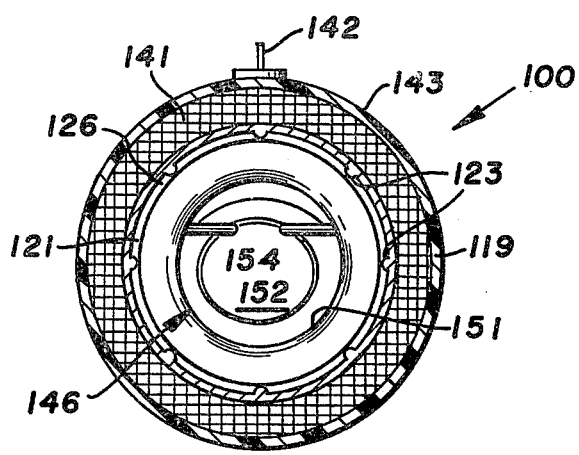
FIG. 8 is a sectional view taken along the line 8—8 of FIG. 7.
Figure 7:
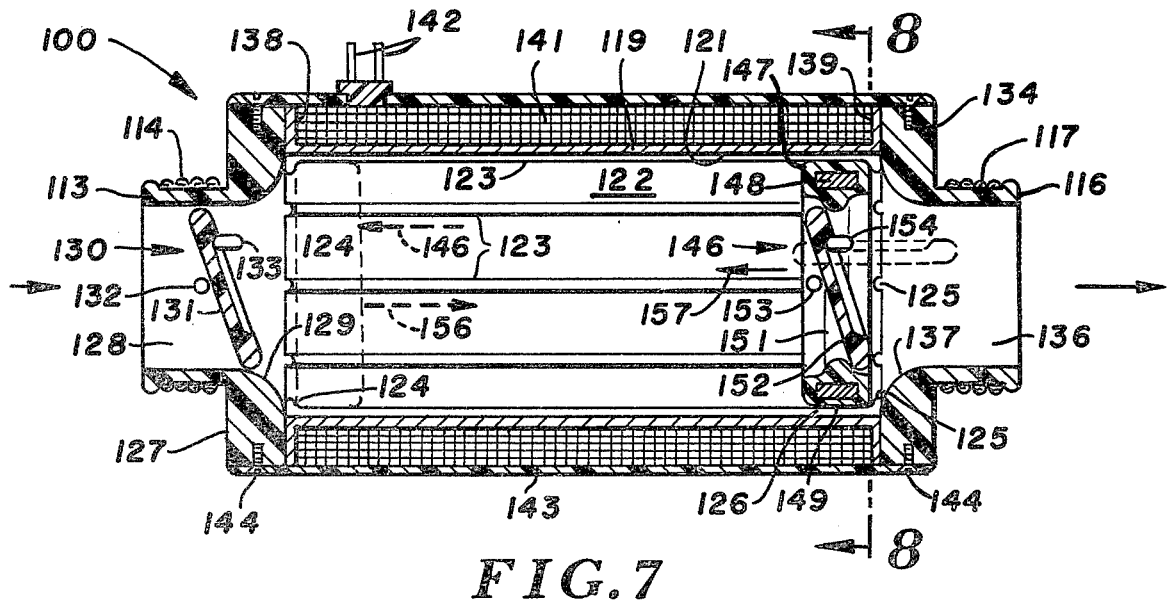
FIG. 7 is an enlarged longitudinal sectional view taken along line 7—7 of FIG. 6.

Referring to FIG. 7, pump 100 has a cylindrical body or casing 119 having an inside wall 121. Wall 121 surrounds a pumping chamber 122. A plurality of longitudinal ribs or veins 123 are integral with the inside surface of wall 119. Ribs 123 extend into the chamber 122 and are circumferentially spaced from each other. Ribs 123 have enlarged terminal ends or stops 124 and 125, as shown in FIG. 8, adjacent ribs 123 and are separated by arcuate spaces 126.

First end member 127 is mounted adjacent one end of body 119. End member 127 has an inlet passage 128 open to chamber 122. Passage 128 has an enlarged cone-shaped exit portion 129 which enhances even laminar flow of fluid into chamber 122.

A one-way valve indicated generally at 130 is located in passage 128 to control the flow of blood through the passage 128. Valve 130 functions to allow blood to flow through passage 128 into chamber 122 and restricts the flow of blood from chamber 122 back through passage 128. Valve 130 has a valving member or a disc 131 pivotally mounted on pairs of pivot member 132 and 133. Disc 131 pivots in an off-center relationship to permit substantial centralized flow of blood into or through passage 128 with chamber 122. Pivot pairs 133 have free end portions that extend into a recess on the distal side of disc 131 to retain disc 131 in a free floating assembled relationship with end member 127. Disc 131 is free to rotate about its central axis as it pivots between its open and closed positions. The outer surface of disc 131 can have a coating or pyrolite carbon, as shown and disclosed with respect to disc 34 in FIG. 3.

A second end member 134 is located adjacent the opposite or right ends of body 119. End member 134 has an outlet passage 136 provided with a cone-shaped inner end that is open to the outlet end of chamber 122. The passage 136 extends through the outlet collar or sleeve 116. The axis of passages 128 and 136 and the chamber 122 are in longitudinal alignment.

Body 119 has annular outwardly directed end flanges 138 and 139 in engagement with the end members 127 and 134, respectively. Flanges 138 and 139 form with the body the cylindrical portion of body 119 an annular recess accommodating a solenoid coil 141, electrical leads 142 are connected to the coil 141. A cylindrical covering or sleeve 143 fits over coil 141 and end members 127 and 134. Fasteners 144, as screws, secure the cover 143 to end members 127 and 134.

Referring to FIGS. 7 and 8, a piston indicated generally at 146 is slidably located in chamber 122 for movement between stops 124 and 125. Piston 146 has an annular body or ring 147 surrounding a core 148 of magnetic material, as iron and the like. Body 147 has a flat cylindrical surface 149 located in sliding engagement with the outer edges of ribs 123. Outer surface 149 is a smooth cylindrical surface allowing the piston to rotate about its axis as it moves between stops 124 and 125. The inside portion of body 127 has an annular lip 151 surrounding a passage through body 147. A one-way valving member or disc 152 located in the passage is operable to control one way flow of blood through the passage in piston 146. A first pair of pivots 153 secured to body 147 in conjunction with a second pair of pivots 154 secured to body 147 pivotally mount disc 152 for movement about an off-center position between open and closed positions. The open position of disc 152 is shown in broken lines in FIG. 7. The passage through body 147 has substantially the same diameter as the diameter of inlet passage 128 and the diameter of outlet passage 136. The entire outer surface of the body 147 and disc 152 can have a coating or skin of pyrolite carbon, as shown in FIG. 3, by the skin on piston 44 and disc 52. The outer or free ends of pivot members 154 extend into a shallow recess in the distal side of disc 52 to hold disc 52 in a free floating assembled relation with the body 147. In other words, disc 52 is free to rotate about its central axis as it moves between its open and closed positions.

In use, when piston 146 is in a first or a dotted line position, as shown in FIG. 7, first valve 130 is closed. When solenoid 141 is energized in a pumping or forward mode the magnetic field created by the solenoid forces piston 146 in a forward direction as indicated by the arrow 156 toward stops 125. The blood in chamber 122 in front of piston 146 will be forced out passage 136. Valve disc 131 moves to the open position allowing additional blood to flow through inlet passage 128 into chamber 122 behind piston 146. Piston 146 continues to move in a forward direction until it engages stops 125. Control 111 then reverses the flow of electric current through solenoid coil 141, thereby creating a reverse flux field. This moves piston 146 in a reverse direction as indicated by the arrow 157 toward the stops 124. When piston 146 is moved in the reverse direction, valve disc 152 opens to the open position as shown in broken lines. This allows the fluid in chamber 122 to move through the passage in body 147 to the opposite or forward side of the piston. Piston 146 continues to move in reverse or to the left, as shown in FIG. 7, back to its initial position, as shown in broken lines. During the reverse movement of the piston 146, valve disc 131 is in its closed position so that the reverse movement of piston 146 does not cause reverse flow of fluid in passage 128. There is a slight reverse or leakage flow of fluid around the outer peripheral edge of disc 131, as the disc 131 is not in a tight sealing relation with the inside wall of the sleeve 113.

The frequency and the speed of movement of piston 146 in chamber 122 is controlled by the magnetic force fields established by solenoid coil 141. Control 111 regulates the electric power supplied to solenoid coil 141, thereby controlling the operating characteristics of piston 146.

Referring to FIGS. 9–12, there is shown a third embodiment of the pump of the invention indicated generally at 200. Pump 200 is an elongated cylindrical member operatively connected to a control 211. A power source 212, such as a battery or an external electric power, is connected to control 211. Lines 230 and 234 electrically couple the control 211 to the pump 200.

Figure 9:
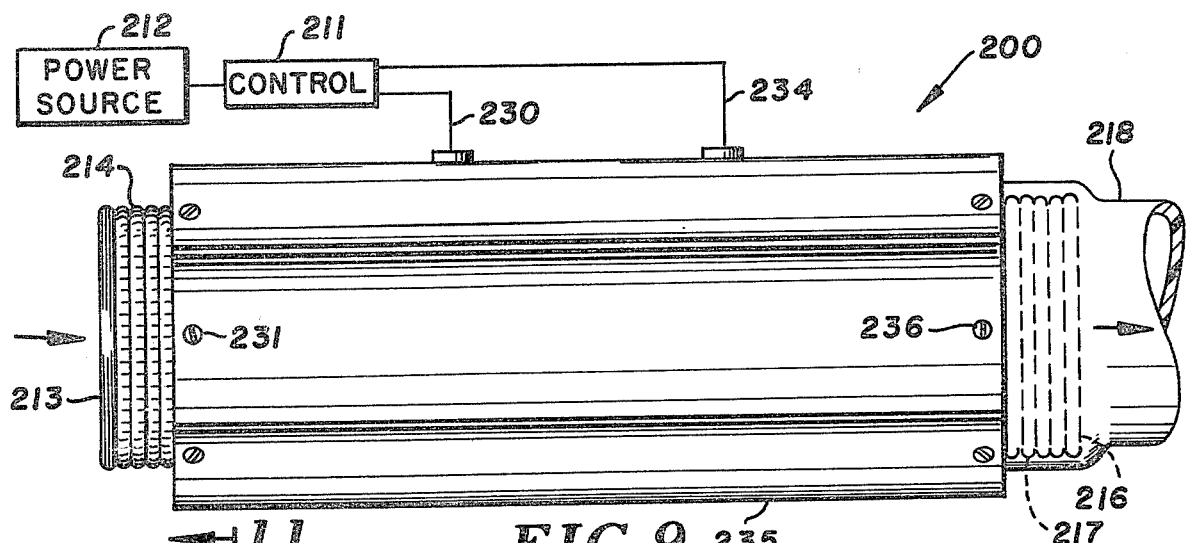
FIG. 9 is a diagrammatic view of a second modification of the pump of the invention connected to a control and power source.
Figure 10:
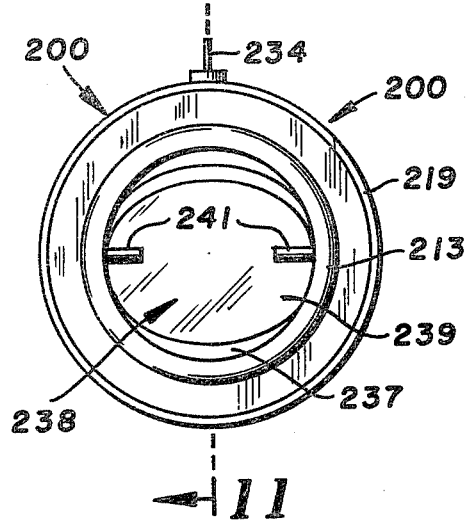
FIG. 10 is an end elevational view of the left end of FIG. 9.

Pump 200 has an inlet collar or sleeve 213 at one end, as shown at the left end of FIG. 9. A suturing ring 214 is mounted on collar 213. The opposite end of pump 200 has an outlet collar 216 carrying a suturing ring 217. An outlet tubular member 218 fits over the suturing ring 217 and is attached thereto with stitches. Tubular member 218 is coupled to the circulatory system of the human or animal. A similar inlet tubular member can be attached to suturing collar 214.

Pump 200 has an elongated body or casing 219 having an inside cylindrical wall 221 forming a pumping chamber 222. An annular inwardly directed ring or stop 224 projects into the left end of chamber 222. The right end of chamber 222 has a groove carrying an annular snap ring 225 forming a second stop.

The outside of body 219 has a first cylindrical groove 228 accommodating a first solenoid coil 229. Electrical lines 230 are connected to coil 229. The opposite end of body 219 has a second cylindrical groove 232 accommodating a second solenoid coil 233. Electrical conductor lines 234 are connected to solenoid coil 233. A cylindrical cover or shell 235 fits over coils 229 and 233. Fasteners 231 and 236 connect opposite ends of cover 235 to body 219.

Body 219 has an inlet or mouth end 237 accommodating a one-way valve indicated generally at 238. Valve 238 has a valving member or disc 239 pivotally mounted about an off-center position on pairs of proximal pivots 241 and pairs of distal pivots 242. Distal pivots 242 have projections at their outer ends that extend into a shallow recess in the distal side of disc 239 to hold the disc in a free floating relationship with respect to body 219. The disc is free to rotate about its longitudinal axis as it moves between its open and closed positions.

A piston assembly indicated generally at 243 is slidably located in chamber 222 between stop members 224 and 225. Piston assembly 243 contains a central ring 244. Ring 244 has an outer surface that is spaced from the inner wall 221 by space 245 to allow continuous flow of blood around ring 244 through space 245. Ring 244 has a central passage 246 accommodating a valving member or disc 247. Pairs of pivots 248 and 249 attached to ring 244 pivotally mount disc 247 on ring 244 for off-center free floating pivotal movement between open and closed positions. Disc 247 is free to rotate about its longitudinal axis as it moves between its open and closed positions. The distal pivots 249 have free ends that extend into a recess in disc 247 to hold disc 247 in assembled relation with ring 244.

Figure 12:
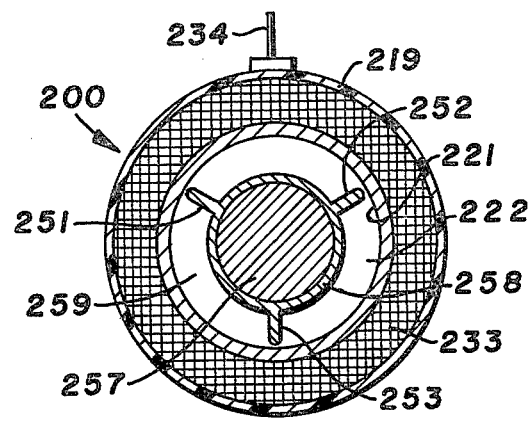
FIG. 12 is a sectional view taken along the line 12—12 of FIG. 11.
Figure 11:
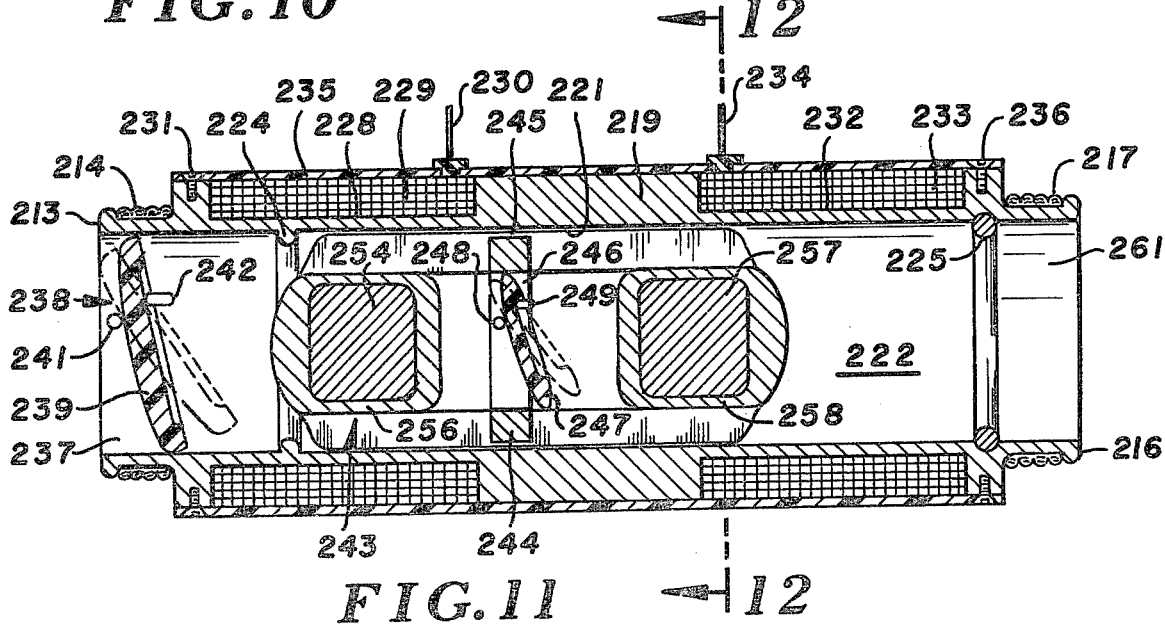
FIG. 11 is a sectional view taken along the line 11—11 of FIG. 10.

A plurality of longitudinal vanes 251, 252, and 253 are attached to disc 244. As shown in FIG. 12, vanes 251, 252, and 253 are circumferentially spaced from each other an equal arcuate distance and have outer edges that engage inside wall 221 of body 219. As shown in FIG. 11, a first core of magnetic material 254 is attached to the outer ends of vanes 251, 252, and 253. Core 254 is covered with a covering or skin 256, as non-magnetic metal, plastic or pyrolite carbon. The opposite or right ends of vanes 251, 252, and 253 are attached to a second core 257 of magnetic material. Core 257 is surrounded with a covering or skin 258 that holds core 257 in assembled relation with vanes 251, 252, and 253. Coverings 256 and 258 are located within the inner edges of the vanes to provide arcuate spaces 259 between coverings 256 and 258 and inside wall 221 of body 219. This allows the fluid to flow past coverings 256 and 258 as piston assembly 243 reciprocates in chamber 222.

In use, piston 243 reciprocates in chamber 222 in response to the flux force fields established by solenoid coils 229 and 233. Control 211 is operable to energize the coil 229 to move piston 243 to the right. This moves the blood in chamber 222 in a forward direction through the outlet passage 261. When piston 243 moves in the forward direction disc 239 pivots to the open position allowing additional fluid to flow into the inlet side of chamber 222. When vanes 251, 252, and 253 engage the forward stop 225 disc 239 moves to the closed position. Solenoid 233 is energized to move piston assembly 243 back to its initial position into engagement with stop 224. Disc 247 moves to the open position so that the blood in the inlet side of chamber 222 moves through passage 246 to the outlet side of chamber 242. Piston assembly 246 reciprocates back and forth in chamber 222 to effect a pulse pumping action of the blood through pump 200.

Control 211 can operate to simultaneously energize the coils 229 and 233 to effect the forward movement of piston assembly 243. The electric circuit of control 211 is operable to reverse the flow of electric power to solenoid coils 229 and 233 to effect a reverse movement of piston assembly 243. Both solenoid coils 229 and 233 can operate together to effect the forward and reverse movements of the piston assembly 243.

There have been shown and described several embodiments of the pump of the invention. It is intended that various changes and modifications can be made by those skilled in the art without departing from the invention.

The embodiments of the invention in which an exclusive property or privilege is claimed are defined as follows:

1. A pump for moving a fluid comprising: a housing including a body having an inside wall surrounding a chamber, a plurality of longitudinal ribs on said inside wall, a first end having inlet passage means open to the chamber, and a second end having outlet passage means open to the chamber; first one-way valving means cooperating with the first end to allow forward flow of fluid through the inlet passage means into the chamber and restrict reverse flow of fluid through the inlet passage means out of the chamber; piston means located in the chamber movable in a forward direction to move fluid out of the chamber through the outlet passage means and allow fluid to flow into the chamber through the inlet passage means and movable in a reverse direction toward the first one-way valving means, said ribs spacing the piston means from the inside wall, said piston means including magnetic means and passage means allowing fluid to flow through the piston means; second one-way valving means movably mounted on the piston means allowing fluid to flow through the passage means in the piston means on reverse movement of the piston means and restricting flow of fluid through the passage means in the piston means on movement of the piston means in the forward direction; and solenoid means mounted on the housing operable to sequentially move the piston means in forward and reverse directions.

2. The pump of claim 1 wherein: the first end of the housing includes a first end member having said inlet passage means, and the second end of the housing includes a second end member, said solenoid means including a first solenoid mounted on the first end member and a second solenoid mounted on the second end member.

3. The pump of claim 2 including: control means connected to the first and second solenoids to energize the first and second solenoids whereby the solenoids cooperate to move the piston means in said chamber.

4. The pump of claim 1 wherein: the first and second one-way valving means each include a movable valving disc.

5. The pump of claim 1 wherein: the solenoid means includes a solenoid located around the body.

6. The pump of claim 5 including: sleeve means located over the solenoid.

7. The pump of claim 1 wherein: the first end of the housing includes a first end member having said inlet passage means located adjacent one end of the body, and the second end of the housing includes a second end member having said outlet passage means located adjacent the other end of the body, said solenoid means including a solenoid surrounding the body and extending between said first and second end members.

8. The pump of claim 7 including: sleeve means surrounding the solenoid and first and second end members, and means securing the sleeve means to the first and second end members.

9. The pump of claim 7 including: control means connected to the solenoid to energize said solenoid whereby the solenoid functions to move the piston means in said chamber.

10. The pump of claim 7 wherein: the first and second one-way valving means each include a movable valving disc.

11. The pump of claim 1 wherein: the solenoid means includes a first solenoid mounted on the housing and a second solenoid mounted on the housing.

12. The pump of claim 11 including: control means connected to the first and second solenoids to energize the first and second solenoids whereby the solenoids cooperate to move the piston means in said chamber.

13. The pump of claim 12 wherein: the first and second one-way valving means each include a movable valving disc.

14. The pump of claim 1 wherein: the first end and second end each have collars for accommodating a suturing member.

15. A pump for moving a fluid comprising: a body having a first end, a second end, and an inside wll surrounding a chamber, a first end member mounted on the first end of the body, said first end member having an inlet passage open to the chamber; first one-way valving means located in the passage allowing fluid to flow through the passage into the chamber and restrict the flow of fluid through the passage out of the chamber; a second end member mounted on the second end of the body, said second member having an outlet passage open to the chamber; a piston located in the chamber, said piston having a passage, said piston having a core of magnetic material; a plurality of longitudinal ribs on the inside wall of the body, said ribs spacing the piston from the inside wall; second one-way valving means mounted on the piston allowing fluid to flow through the piston passage on movement of the piston toward the first end member and restricting the flow of fluid through the piston passage on movement of the piston toward the second end member; and solenoid means operable to move the piston in the chamber to move fluid through the chamber.

16. The pump of claim 15 wherein: the solenoid means comprises a first solenoid mounted on the first end member and a second solenoid mounted on the second end member.

17. The pump of claim 15 wherein: the one-way valving means located in the passage of the first end member includes a disc and means pivotally mounting the disc on the first end member.

18. The pump of claim 15 wherein: the first and second end members each have collars for accommodating a suturing member.

19. The pump of claim 15 wherein: each end member has an annular groove, said solenoid means comprising a first solenoid located in one annular groove and a second solenoid located in the other annular groove.

20. The pump of claim 15 wherein: the second one-way valving means mounted on the piston includes a disc and means pivotally mounting the disc on the piston.

21. The pump of claim 15 including: control means connected to the solenoid means to energize said solenoid means whereby the solenoid means function to move the piston in said chamber.

22. The pump of claim 15 wherein: the solenoid means includes a first solenoid and a second solenoid, and control means connected to the first and second solenoids to energize said first and second solenoids whereby the solenoids cooperate to move the piston in said chamber.

23. The pump of claim 15 including: stop means on the housing engageable with the piston to limit the amount of linear movement of the piston in the chamber.

24. The pump of claim 15 including: stop means on the opposite ends of the ribs engageable with the piston to limit the linear movement of the piston in the chamber.

25. A pump for moving a fluid comprising: housing means including a body having an inside wall surrounding a chamber, first end means having inlet passage means open to the chamber, and second end means having outlet passage means open to the chamber; first one-way valving means located in the inlet passage means to allow forward flow of fluid through the inlet passage means into the chamber and restrict reverse flow of fluid through the inlet passage means out of the chamber, means movably mounting the first one-way valving means on said first end means; piston means located in the chamber movable in a forward direction to move fluid out of the chamber through the outlet passage means and allow fluid to flow into the chamber through the inlet passage means, said piston means being movable in a reverse direction toward the first one-way valving means, said piston means including a magnetic means and passage means allowing the fluid to flow through the piston means during movement thereof in said reverse direction; longitudinal rib means between said inside wall and piston means allowing limited flow of fluid between the piston means and said inside wall during movement of the piston means in said chamber; second one-way valving means movably mounted on the piston means allowing fluid to flow through the passage means in the piston means on reverse movement of the piston means and restricting flow of fluid through the passage means in the piston means on movement of the piston means in the forward direction; means movably mounting the second one-way valving means on the piston means and solenoid means associated with the housing means operable to sequentially move the piston means in the forward and reverse directions.

26. The pump of claim 25 wherein: said solenoid means includes a first solenoid mounted to the housing means and a second solenoid spaced from the first solenoid mounted on the housing means.

27. The pump of claim 26 including: control means connected to the first and second solenoids to energize the first and second solenoids whereby the first and second solenoids cooperate to move the piston means in said chamber.

28. The pump of claim 25 wherein: said first and second one-way valving means each include a pivoting disc, said means mounting the first one-way valving means in the first end means including first pivot means for pivotally retaining a disc in said inlet passage means, and said means mounting the second one-way valving means on the piston means including second pivot means for pivotally retaining a disc on the piston means.

29. The pump of claim 25 wherein: said rib means include a plurality of ribs on the inside wall of the body, said ribs spacing the piston means from said inside wall.

30. The pump of claim 29 including: stop means on the opposite ends of the ribs engageable with the piston means to limit the linear movement of the piston means in the chamber.

31. The pump of claim 25 including: stop means on the housing engageable with the piston means to limit the amount of linear movement of the piston means in the chamber.

32. The pump of claim 25 wherein: said body means has groove means for accommodating the solenoid means, and means surrounding the solenoid means.

33. The pump of claim 25 wherein: each end means has an annular groove, said solenoid means comprising a first solenoid located in one annular groove and a second solenoid located in the other annular groove.

34. The pump of claim 33 wherein: said body means has end portions covering the first and second solenoid means located in said one and other annular grooves.

35. The pump of claim 25 wherein: said first and second end means each have collars for accommodating a suturing member.

36. The pump of claim 25 wherein: said piston means has a ring with an opening allowing fluid to flow through the ring, said second one-way valving means being movably mounted on said ring and operable to allow one-way flow of fluid through said opening.

37. The pump of claim 36 wherein: said magnetic means comprise two magnetic members located on opposite sides of said ring.

38. The pump of claim 36 wherein: said rib means include a plurality of longitudinal members connected to the core means with the ring, each member having an outer edge adapted to engage the inside wall of the housing.

* * * * *

UNITED STATES PATENT AND TRADEMARK OFFICE
CERTIFICATE OF CORRECTION

PATENT NO. : 4,210,409
DATED : July 1, 1980
INVENTOR(S) : Frank W. Child

It is certified that error appears in the above–identified patent and that said Letters Patent are hereby corrected as shown below:

On the title page, the title should be --SOLENOID OPERATED PUMP-- rather than "SOLENOID OPERATING PUMP"

Column 3, line 47, "member" should be --members--.

Column 5, line 7, "member" should be --members--.

Column 5, line 16, "or" should be --of--.

Column 9, line 15, "wll" should be --wall--.

Signed and Sealed this

Second Day of September 1980

[SEAL]

Attest:

SIDNEY A. DIAMOND

Attesting Officer

Commissioner of Patents and Trademarks